United States Patent
Nakamura et al.

(10) Patent No.: US 10,859,477 B2
(45) Date of Patent: Dec. 8, 2020

(54) BIOSEPARATION COMPOSITIONS AND METHODS FOR MAKING AND USING SAME

(71) Applicant: 3M INNOVATIVE PROPERTIES COMPANY, St. Paul, MN (US)

(72) Inventors: Masayuki Nakamura, Woodbury, MN (US); Naota Sugiyama, Hachiouji (JP); Cynthia D. Zook, Hudson, WI (US); Stephen E. Amos, Minneapolis, MN (US); Jerald K. Rasmussen, Woodville, WI (US); Nicole M. Gryska, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 41 days.

(21) Appl. No.: 15/414,265

(22) Filed: Jan. 24, 2017

(65) Prior Publication Data
US 2017/0131190 A1    May 11, 2017

Related U.S. Application Data

(62) Division of application No. 14/367,093, filed as application No. PCT/US2012/070007 on Dec. 17, 2012, now abandoned.

(60) Provisional application No. 61/578,315, filed on Dec. 21, 2011.

(51) Int. Cl.

| | |
|---|---|
| *G01N 1/00* | (2006.01) |
| *G01N 1/40* | (2006.01) |
| *B01J 20/28* | (2006.01) |
| *B01D 15/38* | (2006.01) |
| *B01J 20/32* | (2006.01) |
| *B01J 20/281* | (2006.01) |
| *B01J 20/289* | (2006.01) |
| *C07K 1/16* | (2006.01) |
| *C12N 15/10* | (2006.01) |

(52) U.S. Cl.
CPC ......... *G01N 1/405* (2013.01); *B01D 15/3804* (2013.01); *B01J 20/281* (2013.01); *B01J 20/28004* (2013.01); *B01J 20/289* (2013.01); *B01J 20/28021* (2013.01); *B01J 20/3204* (2013.01); *B01J 20/3219* (2013.01); *B01J 20/3248* (2013.01); *B01J 20/3261* (2013.01); *B01J 20/3291* (2013.01); *C07K 1/16* (2013.01); *C12N 15/101* (2013.01); *C12N 15/1006* (2013.01); *B01J 2220/82* (2013.01)

(58) Field of Classification Search
CPC ...................................................... G01N 1/405
USPC ...................................................... 436/178
See application file for complete search history.

(56) References Cited

U.S. PATENT DOCUMENTS

| | | | |
|---|---|---|---|
| 4,391,930 A | | 7/1983 | Olson |
| 4,937,209 A | * | 6/1990 | Jones ................. B01J 20/16 435/176 |
| 5,866,006 A | * | 2/1999 | Lihme ............... B01D 15/1807 210/198.2 |
| 2001/0029050 A1 | * | 10/2001 | Starzl ................ G01N 33/525 436/518 |
| 2007/0015191 A1 | | 1/2007 | Bitner |
| 2009/0176201 A1 | | 7/2009 | Jablonski |
| 2010/0184913 A1 | | 7/2010 | Ebbrecht et al. |

FOREIGN PATENT DOCUMENTS

| | | |
|---|---|---|
| EP | 0051823 | 5/1982 |
| WO | WO 2005-108625 | 11/2005 |
| WO | WO 2006-137933 | 12/2006 |
| WO | WO 2010-090596 | 8/2010 |
| WO | WO 2011-135480 | 11/2011 |

OTHER PUBLICATIONS

International Search Report for PCT International Application No. PCT/US2012/070007, dated May 31, 2013, 6 pages.
Stefansson, et al., "Sample preparation using buoyant silica microspheres" in Proceedings of the 6th Early Detection Research Network Workshop, Creatv MicroTech, Inc., Bethesda, MD, USA, Aug. 31-Sep. 3, 2009, 1 page.

* cited by examiner

*Primary Examiner* — Lyle Alexander
*Assistant Examiner* — Emily R. Berkeley
(74) *Attorney, Agent, or Firm* — Qiang Han

(57) ABSTRACT

A composition for use in bioseparation. The composition includes a plurality of hollow particles having a siliceous surface. The composition further includes a surface-modifying agent bonded to the hollow particles. The surface-modifying agent includes a binding segment and a reactive segment. The binding segment includes a silyl group and the reactive segment includes a reactive nitrogen group.

5 Claims, No Drawings

US 10,859,477 B2

BIOSEPARATION COMPOSITIONS AND METHODS FOR MAKING AND USING SAME

FIELD

The present disclosure relates to compositions and methods useful for separating biomaterial from a sample.

BACKGROUND

Various particles have been introduced into samples to separate biomaterial from such samples. Various particles for biomaterial separation are described, for example, in U.S. Pat. App. Pub. No. 2009/0176201 (Jablonski et al.) and U.S. Pat. App. Pub. No. 2007/0015191 (Bitner et al.).

SUMMARY

In some embodiments, a composition for use in bioseparation is provided. The composition comprises a plurality of hollow particles having a siliceous surface. The composition further comprises a surface-modifying agent bonded to the hollow particles. The surface-modifying agent comprises a binding segment and a reactive segment. The binding segment comprises a silyl group and the reactive segment comprises a reactive nitrogen group. The plurality of hollow particles have an average density between about 0.05 and 0.4 g/ml.

In some embodiments, a method for making a bioseparation composition is provided. The method comprises size fractionating a first plurality of hollow particles having a first particle size distribution with a first span to form a second plurality of hollow particles having a second particle size distribution with a second span that is less than the first span. The method further comprises surface-modifying either or both of the first and second plurality of hollow particles with a surface modifying agent to form surface-modified hollow particles. The surface-modifying agent comprises a binding segment and a reactive segment. The binding segment comprises a silyl group and the reactive segment comprises a reactive nitrogen group.

In some embodiments, a method for capturing an analyte is provided. The method comprises providing a bioseparation composition. The bioseparation composition comprises a plurality of hollow particles having a siliceous surface. The composition further comprises a surface-modifying agent bonded to the hollow particles. The surface-modifying agent comprises a binding segment and a reactive segment. The binding segment comprises a silyl group and the reactive segment comprises a reactive nitrogen group. The plurality of hollow particles have an average density between about 0.05 and 0.4 g/ml. The method further comprises contacting the bioseparation composition with a solution comprising an analyte.

The above summary of the present disclosure is not intended to describe each embodiment of the present invention. The details of one or more embodiments of the disclosure are also set forth in the description below. Other features, objects, and advantages of the invention will be apparent from the description and from the claims.

DETAILED DESCRIPTION

Use of various types of particles to absorb or bind to biomaterials of interest (e.g., cells, viruses, bacteria, proteins, nucleic acids) for the purpose of isolating such biomaterials is known. Typical isolation processes involve the introduction of particles into a sample (e.g., a solution) containing a biomaterial target, agitation of the sample, attachment of the biomaterial target to the particles, and subsequent separation of the particles from the sample. Separation of the particles, using known particle compositions, however, is time consuming and/or requires additional processing steps (e.g., centrifugation, filtration).

DEFINITIONS

As used herein, the term "bubble," refers to a small, hollow globule, for example, a small spherical volume of gas encased within a thin film.

As used herein, the term "analyte," refers to any substance which may be present in a sample, and that it is desirable to separate from the sample or to detect in an assay. The analyte can be, without limitation, any substance. For example, an analyte may comprise a substance for which there exists a naturally occurring antibody or for which an antibody can be prepared. The analyte may, for example, be a protein, a polypeptide, a hapten, a carbohydrate, a lipid, a drug, a bacterium, a virus, an enzyme, a cell, a cellular subcomponent or organelle (e.g., lysozomes, mitochondria) or any other of a wide variety of biological or non-biological molecules, complexes or combinations thereof. In still another example, the analyte is a nucleic acid (DNA, RNA, PNA and nucleic acids that are mixtures thereof or that include nucleotide derivatives or analogs).

As used herein, the term "alkyl" refers to a monovalent group that is a radical of an alkane and includes groups that are linear, branched, cyclic, bicyclic, or a combination thereof. The alkyl group typically has 1 to 30 carbon atoms. In some embodiments, the alkyl group contains 1 to 20 carbon atoms, 1 to 10 carbon atoms, 1 to 6 carbon atoms, 1 to 4 carbon atoms, or 1 to 3 carbon atoms. In some embodiments, the alkyl group contains one or more heteroatoms, such as oxygen, nitrogen, or sulfur atoms.

As used herein, the term "alkylene" refers to a divalent group that is a radical of an alkane and includes groups that are linear, branched, cyclic, bicyclic, or a combination thereof. The alkylene group typically has 1 to 30 carbon atoms. In some embodiments, the alkylene group has 1 to 20 carbon atoms, 1 to 10 carbon atoms, 1 to 6 carbon atoms, or 1 to 4 carbon atoms. In some embodiments, the alkylene group contains one or more heteroatoms, such as oxygen, nitrogen, or sulfur atoms.

As used herein, the term "alkyleneoxy" refers to a divalent group that is an oxy group bonded directly to an alkylene group.

As used herein, the term "alkoxy" refers to a monovalent group having an oxy group bonded directly to an alkyl group.

As used herein, the term "aryl" refers to a monovalent group that is aromatic or heteroaromatic. The aryl has at least one unsaturated carbocyclic or heterocyclic ring and can have one or more additional fused rings that can be unsaturated, partially saturated, or saturated. Aryl groups often have 6 to 20 carbon atoms, 6 to 18 carbon atoms, 6 to 16 carbon atoms, 6 to 12 carbon atoms, or 6 to 10 carbon atoms, and 0 to 5 heteroatoms selected from oxygen, sulfur, or nitrogen.

As used herein, the term "arylene" refers to a divalent group that is aromatic or heteroaromatic. The arylene has at least one unsaturated carbocyclic or heterocyclic ring and can have one or more additional fused rings that can be unsaturated, partially saturated, or saturated. Arylene groups often have 6 to 20 carbon atoms, 6 to 18 carbon atoms, 6 to 16 carbon atoms, 6 to 12 carbon atoms, or 6 to 10 carbon atoms, and 0 to 5 heteroatoms selected from oxygen, sulfur, or nitrogen.

As used herein, the term "aryloxy" refers to a monovalent group having an oxy group bonded directly to an aryl group.

As used herein, the term "aralkyl" refers to a monovalent group that is an alkyl group substituted with an aryl group. Aralkyl groups often have an alkyl portion with 1 to 10 carbon atoms, 1 to 6 carbon atoms, or 1 to 4 carbon atoms and an aryl portion with 6 to 20 carbon atoms, 6 to 18 carbon atoms, 6 to 16 carbon atoms, 6 to 12 carbon atoms, or 6 to 10 carbon atoms.

As used herein, the term "aralkyloxy" refers to a monovalent group having an oxy group bonded directly to an aralkyl group. Equivalently, it can be considered to be an alkoxy group substituted with an aryl group.

As used herein, the term "aralkylene" refers to a divalent group that is an alkylene group substituted with an aryl group or an alkylene group attached to an arylene group. Aralkylene groups often have an alkylene portion with 1 to 10 carbon atoms, 1 to 6 carbon atoms, or 1 to 4 carbon atoms and an aryl or arylene portion with 6 to 20 carbon atoms, 6 to 18 carbon atoms, 6 to 16 carbon atoms, 6 to 12 carbon atoms, or 6 to 10 carbon atoms.

As used herein, the term "acyloxy" refers to a monovalent group of formula —O(CO)$R^b$ where $R^b$ is alkyl, aryl, or aralkyl. Suitable alkyl $R^b$ groups often have 1 to 10 carbon atoms, 1 to 6 carbon atoms, or 1 to 4 carbon atoms. Suitable aryl $R^b$ groups often have 2 to 12 carbon atoms and 0 to 3 heteroatoms, such as, for example, phenyl, furyl, or imidazolyl. Suitable aralkyl $R^b$ groups often have an alkyl group with 1 to 10 carbon atoms, 1 to 6 carbon atoms, or 1 to 4 carbon atoms that is substituted with an aryl having 6 to 12 carbon atoms such as, for example, phenyl.

As used herein, the term "hydrolyzable group" refers to a group that can react with water having a pH of 1 to 10 under conditions of atmospheric pressure. The hydrolyzable group is often converted to a hydroxyl group when it reacts. The hydroxyl group often undergoes further reactions. Typical hydrolyzable groups include, but are not limited to, alkoxy, aryloxy, aralkyloxy, acyloxy, or halo. As used herein, the term is often used in reference to one of more groups bonded to a silicon atom in a silyl group.

As used herein, the term "non-hydrolyzable group" refers to a group that cannot react with water having a pH of 1 to 10 under conditions of atmospheric pressure. Typical non-hydrolyzable groups include, but are not limited to alkyl, aryl, and aralkyl.

As used herein, the singular forms "a", "an", and "the" include plural referents unless the content clearly dictates otherwise. As used in this specification and the appended embodiments, the term "or" is generally employed in its sense including "and/or" unless the content clearly dictates otherwise.

As used herein, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

In some embodiments, the present disclosure relates to compositions for use in bioseparation (e.g., isolating and/or assaying analytes). The compositions may include particles and one or more surface-modifying agents bonded to the particles.

In various embodiments, particles useful in the compositions of the present disclosure may include hollow particles having an at least partially solid outer region (e.g., shell) and a hollow inner region (e.g., core). For example, in some embodiments, useful particles may include bubbles having a substantially spherical hollow inner region encased by an outer region. The hollow inner region of the bubbles may be void of fluid, or be filled with a gas, including, but not limited to oxygen, nitrogen, carbon dioxide, helium, fluorocarbon gases and various combinations thereof, such as air. The outer region may be any material that can encase a volume of fluid, for example, a solid such as a metal, glass, ceramic, or similar material. In some embodiments, the outer region may include a siliceous material having a siliceous surface (e.g., for bonding to a surface-modifying agent). In one embodiment, the hollow particles may include glass bubbles, such as those sold by 3M under the trade designation SCOTCHLITE™ Glass Bubbles.

Generally, the particles of the present disclosure may be configured and/or sized to facilitate rapid separation from a solution (e.g., based on buoyancy forces). The particles may have an average density of less than about 1 g/ml, less than about 0.8 g/ml, less than about 0.6 g/ml, or even less than about 0.4 g/ml. In some embodiments, the particles may have an average density in a range of from about 0.05 g/ml to about 0.8 g/ml, or from about 0.08 g/ml to about 0.4 g/ml. The particles may have a mean particle size of less than about 200 micrometers, less than about 100 micrometers, or even less than about 80 micrometers. In illustrative embodiments, the particles may have a mean particle size in a range of from about 5 to 250 micrometers, from about 10 to 100 micrometers, or from about 20 to 80 micrometers.

Typically, commercially available particles suitable for use as a raw material for the bioseparation compositions of the present disclosure exhibit a relatively broad particle size distribution. Surprising and advantageously, it was discovered that particle compositions having a narrower particle distribution more rapidly separate from a solution. In this regard, as will be described in further detail below, the particles useful in the compositions of the present disclosure may be a collection of particles that have been size fractionated (i.e., isolated based on size) from a larger collection of particles to achieve a desired particle size distribution.

There are many ways to describe the width of a particle size distribution. In one method, the width of a particle size distribution can be expressed by the following formula:

$$\frac{90P - 10P}{50P} = GQ = \text{span}$$

wherein 90P is the size for which 90 percent of the particles in the distribution are smaller (referred to as the 90th percentile size); 10P is the size for which only 10 percent of the particles in the distribution are smaller (referred to as the 10th percentile size); 50P is the size for which 50 percent of the particles in the distribution are smaller (referred to as the 50th percentile size); and GQ stands for the gradation quotient. The gradation quotient is also commonly known in the art by the term "span".

In some embodiments, the particles useful in the bioseparation compositions of the present disclosure may have a size distribution with a span of less than about 1, less than about 0.8, less than about 0.7, less than about 0.65, or even less than about 0.5. The particles may have a size distribution with a span in a range of from about 0.1 to 1, from about 0.2 to 0.8, or from about 0.3 to 0.75.

Generally, the surface-modifying agents of the present disclosure may include any molecules capable of coupling to particles useful for bioseparation (e.g., via covalent interactions, ionic interactions, hydrophobic interactions, or combinations thereof), and following such particle coupling, coupling to one or more analytes (e.g., via covalent interactions, ionic interactions, hydrophobic interactions, or combinations thereof) such that the analytes may be separated from a sample. In various embodiments, the surface-modifying agents of the present disclosure may include at least a binding segment, a linking segment, and a reactive segment:

Binding Segment-Linking Segment-Reactive Segment

Generally, the binding segment may include any segment capable of bonding the surface-modifying agent to the particles. The bond may be achieved, for example, covalently, hydrophobically, ionically, or combinations thereof. In some embodiments, the binding segment may include a silyl group, e.g., binding segments having a formula:

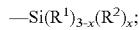
—Si($R^1$)$_{3-x}$($R^2$)$_x$;

where x=0, 1, or 2;

each group $R^1$ includes independently $OH^-$ or a hydrolyzable group from among halo, alkoxy, aryloxy, aralkyoxy, and acyloxy; and each group $R^2$ includes independently a non-hydrolyzable group from among alkyl, aryl, and aralkyl.

Generally, the linking group may include any segment suitable for connecting the binding segment with the reactive segment. In illustrative embodiments, the linking segment may comprise alkylene, arylene, or both, and optionally further comprises —NH— or alkyleneoxy, or both.

Generally, the reactive segment may include any segment capable of coupling to one or more analytes such that the analyte may be separated from a sample (e.g., a solution having an analyte dispersed therein). In some embodiments, the reactive segment may include a reactive nitrogen group, e.g., reactive segments having a formula:

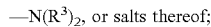
—N($R^3$)$_2$, or salts thereof;

where each group $R^3$ comprises independently hydrogen, alkyl, aryl, or aralkyl In some embodiments, the surface-modifying agent may include (aminoethylaminomethyl)phenethyltrimethoxysilane (SIA0588.0, available from Gelest, Inc., Tullytown, Pa.), N-(2-aminoethyl)-3-aminopropylmethyldimethoxysilane (SIA0589.0, Gelest), N-(2-aminoethyl)-3-aminopropyltrimethoxysilane (SIA0591.0, Gelest), N-(6-aminohexyl)aminopropyltrimethoxysilane (SIA0594.0, Gelest), N-(2-aminoethyl)-11-aminoundecyl-trimethoxysilane (SIA0595.0, Gelest), aminophenyltrimethoxysilane (SIA0599.2, Gelest), N-3-[(amino(polypropylenoxy)]aminopropyltrimethoxysilane (SIA0599.4, Gelest), 3-aminopropyldimethylethoxysilane (SIA0603.0, Gelest), 3-aminopropylmethyldiethoxysilane (SIA0605.0, Gelest), aminopropylsilanetriol (SIA0608.0, Gelest), 3-aminopropyltriethoxysilane (SIA0610.0, Gelest), 3-aminopropyltrimethoxysilane (SIA0611.0, Gelest), n-butylaminopropyltrimethoxysilane (SIB1932.2, Gelest), N-methylaminopropylmethyldimethoxysilane (SIM6498.0, Gelest), N-methylaminopropyltrimethoxysilane (SIM6500.0, Gelest), N-(trimethoxysilylethyl)-benzyl-N,N,N-trimethylammonium chloride (SIT8395.0, Gelest), 2-(trimethoxysilylethyl)pyridine (SIT8396.0, Gelest), (3-trimethoxysilylpropyl)diethylene-triamine (SIT8398.0, Gelest), and combinations thereof.

In further embodiments, the present disclosure may relate to a method of making bioseparation compositions (e.g., the bioseparation compositions described above). The method may include size fractionating a first volume of particles to yield a second volume of particles having a desired particle size distribution. Any conventional size fractionation method may be employed including filtration, decantation, sedimentation, centrifugation, wet or dry screening, air or liquid elutriation, cyclones, static electricity, or combinations thereof. In some embodiments, size fractionating yields a second volume of particles having a particle size distribution that is narrower than the particle size distribution of the first volume. Size fractionating may yield a second volume of particles having a particle size distribution with a span of less than about 1, less than about 0.8, less than about 0.7, less than about 0.6, or even less than about 0.5.

Prior to, simultaneous with, or following the step of size fractionating, in some embodiments, the method may further include surface modifying at least a portion of the particles. In some embodiments, surface modifying may include subjecting the particles to an optional pre-treatment step (e.g., to expose or clean a surface of the particle to facilitate surface modification). The optional pre-treatment step may include an alkaline treatment. Alternatively, or additionally, the pretreatment may include an acid or plasma cleaning treatment.

Following any optional pre-treatment step, the method may include introducing the particles into a treatment solution that includes one or more surface-modifying agents and one or more solvents, thereby producing particles having the surface-modifying agents bonded to or otherwise exhibited on the exterior surface of the particles (i.e., surface-modified particles). The surface-modification treatment solution may be agitated (stirred, shaken, etc.) and/or temperature controlled (e.g., heated) to facilitate surface modification of the particles.

In various embodiments, the surface-modification treatment solution may include one or more solvents (e.g., organic and inorganic liquids (including water) or plasticizers known to be used or useful to dissolve or soften other organic or inorganic materials) and one or more surface-modifying agents. The treatment solution may include at least 0.01 wt. %, at least 0.04 wt. %, at least 0.1 wt. %, at least 1.0 wt. %, at least 4.0 wt. %, or even at least 10 wt. % of surface-modifying agent, based on the total weight of the surface-modification treatment solution.

In some embodiments, the ratio of surface-modification treatment solution to particles may vary widely. This ratio, and the concentration of the surface-modifying agent in the treatment solution, can be used to control the amount of modifying agent that is coupled to the particles. Generally, the amount of surface-modification treatment solution may be at least enough to wet the surface of the particles, or may be enough to allow for dispersion of the particles in the solution, thus allowing for agitation during the treatment process. In illustrative embodiments, the ratio of surface-modification treatment solution to particles may be at least 0.25:1, at least 0.5:1, at least 1:1, at least 2:1, at least 5:1, or even at least 10:1, on a volume basis.

In some embodiments, following surface modification of the particles in a treatment solution, the surface-modified particles may be separated from the treatment solution (e.g., by filtration), optionally washed, and dried.

In yet another embodiment, the present disclosure may relate to a method for capturing an analyte in a solution. The method may include providing surface-modified particles, and contacting the surface-modified particles with a solution having one or more analytes capable of coupling to (or otherwise capable of being captured by) the surface-modifying agent, thereby generating surface-modified particles carrying an analyte. The method may further include agitating (e.g., inverting, stirring, shaking, etc.) the solution to achieve dispersion of the surface-modified particles throughout the solution. In some embodiments, the solution may be agitated such that the surface-modified particles are substantially uniformly dispersed throughout the solution.

In some embodiments, the method may also include separating the analyte-carrying surface-modified particles from the solution. Generally, any known methods for separating particles from a solution may be employed. In some embodiments, separating the particles from the solution may include allowing the analyte carrying surface-modified particles to float to an upper surface (i.e., air/solution interface) of the solution.

The surface-modified hollow particles of the present disclosure may facilitate rapid separation of the particles from the solution. For example, in embodiments in which the particles are separated by flotation to an upper surface of the solution, the particles of the present disclosure may separate in less than about 2 minutes, less than about 1 minute, less than about 30 seconds, or even less than about 15 seconds. In this manner, all manner of analytes may be readily captured by the surface-modified particles of the present disclosure. In illustrative embodiments, the method may include capture of one or more proteins and/or one or more nucleic acids from a solution utilizing the surface-modified particles of the present disclosure.

In some embodiments, the compositions and methods of the present disclosure may be useful in, for example, food pathogen detection, medical diagnostics, cell separation, and environmental monitoring and/or cleaning.

EXAMPLES

The operation of the present disclosure will be further described with regard to the following detailed examples. These examples are offered to further illustrate the various specific and preferred embodiments and techniques. It should be understood, however, that many variations and modifications may be made while remaining within the scope of the present disclosure.

As used herein, all percentages are by weight unless indicated otherwise.
Materials used in Examples
Glass Bubbles (GB1-GB5)
GB1—K25 3M™ Glass Bubbles—density of 0.25 g/mL, average diameter of 51 micrometers (µm), span of 1.12 (3M Company; St. Paul, Minn.)
GB2—XLD3000 3M™ Glass Bubbles—density of 0.23 g/mL, average diameter of 30, (µm), span of 0.9 (3M Company)
GB3—XLD6000 3M Glass Bubbles—density of 0.3 g/mL, average diameter of 17.6 micrometers (µm), span of 0.74 (3M Company)
GB4—iM30K 3M™ Glass Bubbles—density of 0.6 g/mL, average diameter of 17 micrometers (µm), span of 1.19 (3M Company)
GB5—S60HS 3M™ Glass Bubbles—density of 0.6 g/mL, average diameter of 30 µm, span of 1.18 (3M Company)
Amino Silanes (AS1-AS5)
AS1—3-aminopropyl-trimethoxysilane—CAS#13822-56-5 (Sigma Aldrich, St. Louis, Mo. (Sigma))
AS2—N'-(3-trimethoxysilylpropyl)diethylenetriamine—CAS#35141-30-1 (Sigma)
AS3—3-(2-aminoethylamino)propyldimethoxymethylsilane—CAS#3069-29-2 (Alfa Aesar, Ward Hill, Mass.)
AS4—N-trimethoxysilylpropyl-N,N,N-trimethylammonium chloride—CAS#35141-36-7 (Gelest; Morrisville, Pa. (Gelest))
AS5—trimethoxysilylpropyl(poly-ethylenimine)—CAS#136856-91-2 (Gelest)
AS6—aminopropyltriethoxy silane CAS#919-30-2 (Dow Corning, Midland, Mich.)
Test Methods
Debris Removal Procedure 50 mg of glass bubbles were suspended in water in a 60 mL disposable syringe, mixed well by inversion, and allowed to float to the top of the suspension. The settling debris (e.g., the fines and shards that settle to the bottom during separation) were removed by draining the bottom liquid layer from the syringe. This removal process was repeated three times. The remaining floating glass bubbles were collected and filtered through a paper filter using an aspirator system, then dried.
Fractionation Procedure 5-10 g of glass bubbles and 400 mL of water were added to a cylindrical separatory funnel, mixed well by inverting the funnel up and down 3-4 times, and secured upright for a period (a "fractionation interval") prior to removal of the liquid phase. During the fractionation interval, the glass bubbles separated into three segments: (i) a top segment floating at the surface of the water in the funnel; (ii) a bottom segment of fines and shards that settled out of the water; and (iii) a middle segment forming a cloudy suspension of water and glass bubbles between the top and bottom segments. The fractionation interval was selected such that these three distinct segments were apparent and was determined empirically for the desired particle size distribution for a given bubble density and diameter. In this regard, the fractionation interval was selected to be relatively short (e.g., 1 minute) in order to drain and remove the bubbles of segments (ii) and (iii). That is, the fractionation period was selected such that it was shorter than the time necessary for the glass bubbles of segment (ii) to rise to the surface of the water in the funnel.

After the fractionation interval, approximately 390 mL of water and glass bubbles was drained from the bottom of the funnel, leaving highly floatable glass bubbles at the surface of the remaining water in the funnel Water was added again to the funnel and the process was repeated 4-5 more times. The remaining glass bubbles were collected and filtered through a paper filter using an aspirator system. The glass bubbles were rinsed with acetone, placed in a vacuum chamber at low pressure (about 10 kPa) to dry overnight, and collected into a glass jar.
Particle Size Distribution and Span Value Procedure Particle size distribution of the glass bubbles was measured by light scattering using a laser particle analyzer (SATURN DIGISIZER™ 5200; Micromeritics; Norcross, Ga.). The fraction of the particles for which 10 percent of the particles in the distribution were smaller (10P), the fraction of the particles for which 50 percent of the particles in the distribution were smaller (50P), and the fraction of the particles for which 90 percent of the particles in the distribution were smaller (90P), were determined from the particle size distribution. The span value was calculated using the 10P, 50P and 90P values using the formula, span=(90P−10P)/50P.

Examples 1-3: Fractionation of Glass Bubbles Prior to Surface Modification

Glass bubbles GB1, GB2, and GB3 were each fractionated in accordance with the Fractionation Procedure. The span values were determined, in accordance with the Particle Size Distribution and Span Value Procedure, before and after fractionation. The results are shown in Table 1.

TABLE 1

Reduced span values by glass bubble fractionation

| | | Original | | Span value | |
|---|---|---|---|---|---|
| Ex | Glass Bubble | Density* (g/mL) | Fractionation interval (min) | Before fractionation | After fractionation |
| 1 | GB1 | 0.25 | 1 | 1.12 | 0.61 |
| 2 | GB2 | 0.23 | 15 | 0.90 | 0.68 |
| 3 | GB3 | 0.3 | 15 | 0.74 | 0.50 |

*Density after fractionation is assumed to be similar to the original density (e.g., +/−10%).

Example 4: Fractionation of Glass Bubbles after Surface Modification

Twenty five pounds of GB4 were placed into a 150 L horizontal fluidized bed mixer chamber with a center shaft having plow shares spinning at 150 RPM to fluidize the glass bubbles in the chamber. The fluidized bed was heat jacketed and the heater was set at 150° F. When the glass bubbles reached approximately 150° F., 0.25 pounds of water was sprayed into the mixer from an atomizing spray lance mounted on the top of the fluidized bed mixer. Immediately after spraying the water, 0.25 pounds of aminopropyltriethoxy silane was sprayed through an atomizing nozzle onto the bubbles. The heater set point was then raised to 250° F. The material was allowed to mix for approximately 20 minutes as the temperature of the mass increased to around the boiling point of water. After about 5 minutes of further mixing, the temperature of the mass started to increase indicating that excess water and ethanol, a by-product of the reaction, had been driven off. The material was then cooled and poured into a plastic bag.

The resulting aminopropyltriethoxy silane coated glass bubbles were fractionated in accordance with the Fractionation Procedure. The particle size and span values were calculated in accordance with the Particle Size Distribution and Span Value Procedure. The results are shown in Table 2.

TABLE 2

Reduced span values by glass bubble fractionation

| | | Original | | Span value | |
|---|---|---|---|---|---|
| Ex | Glass Bubble | Density* (g/mL) | Fractionation interval (min) | Before fractionation | After fractionation |
| 4 | GB4 | 0.6 | 12 | 1.19 | 0.76 |

*Density after fraction is assumed to be similar to the original density (e.g., +/−10%).

Example 5, Comparative Examples C1-C2: Effect of Debris Removal Vs. Fractionation on Separation Time For Example 5, a sample of GB1 was fractionated in accordance with the Fractionation Procedure. For Comparative Examples C1 and C2, samples of GB1 and GB5, respectively, were subjected to the Debris Removal Procedure.

Separation time was determined by mixing 0.05 mL of each sample with 3 mL of DI water in a glass vial (14 mm inner diameter, water height of 30 mm), and placing upright to allow the suspension to separate. Separation time, determined as the time for substantially all of the glass bubbles to float to the top surface of the water, was measured. The results are shown in Table 3.

TABLE 3

Separation time comparison

| Example | Glass Bubbles | Separation time |
|---|---|---|
| 5 | GB1 (fractionated) | 15 seconds |
| C1 | GB1 (debris removed) | 2 minutes |
| C2 | GB5 (debris removed) | 10 minutes |

Example 6-19, Reference Examples R1-R2: Preparation of Amine-Modified Glass Bubbles GB1 glass bubbles were fractionated in accordance with the Fractionation Procedure. Approximately 3 grams of the fractionated glass bubbles were added to 100 mL of 0.01 N or 0.1 N sodium hydroxide in a glass jar. The jar was placed on a shaker for at least 6 hours and the bubbles were drained and dried. For Examples 6-11, 0.5 g of the alkaline treated glass bubbles were added to 20 g of a mixture of 95 wt % ethanol and 5 wt % water, and the pH was adjusted to 5.0 with acetic acid. For Examples 12-19, 0.03 g of the alkaline treated glass bubbles were added to 4 g of a mixture of 95 wt % ethanol and 5 wt % water, and the pH was adjusted to 5.0 with acetic acid. An aminosilane in the amount shown in Table 4 was added to all these mixtures and each jar was placed on a shaker at room temperature for at least one hour. After shaking, the glass bubbles were collected and filtered through a paper filter using an aspirator. The bubbles were rinsed with acetone, placed in a vacuum chamber to dry at low pressure (about 10 kPa) overnight, and then stored in a glass jar.

TABLE 4

Amino-silane modifying of fractionated GB1 glass bubbles

| Ex | Alkaline condition | Amino-silane | mg of amino-silane per g of 95% ethanol solution |
|---|---|---|---|
| 6  | 0.01N NaOH | AS1 | 0.45 |
| 7  | 0.01N NaOH | AS1 | 4.5 |
| 8  | 0.01N NaOH | AS1 | 45 |
| 9  | 0.1N NaOH  | AS1 | 0.45 |
| 10 | 0.1N NaOH  | AS1 | 4.5 |
| 11 | 0.1N NaOH  | AS1 | 45 |
| 12 | 0.1N NaOH  | AS2 | 25 |
| 13 | 0.1N NaOH  | AS2 | 2.5 |
| 14 | 0.1N NaOH  | AS3 | 25 |
| 15 | 0.1N NaOH  | AS3 | 2.5 |
| 16 | 0.1N NaOH  | AS4 | 25 |
| 17 | 0.1N NaOH  | AS4 | 2.5 |
| 18 | 0.1N NaOH  | AS5 | 25 |
| 19 | 0.1N NaOH  | AS5 | 2.5 |
| R1 | 0.01N NaOH | n/a | Not treated |
| R2 | 0.1N NaOH  | n/a | Not treated |

Examples 20-25 and Reference Examples R3-R4: DNA Capture by Amine-Modified Glass Bubbles Aminosilane modified, fractionated glass bubbles from Examples 6-11 and unmodified, fractionated glass bubbles from Example 1 were tested for DNA capture by mixing 10 milligrams of the glass bubbles with 1.5 mL of 9 μg/mL of calf thymus DNA (Sigma-Aldrich) in PBS (Phosphate buffered saline, pH 7.0, Sigma) in a centrifuge tube. The tubes were inverted up and down repeatedly for 1 minute at room temperature. The tubes were placed upright for about 10 seconds for the glass bubbles to float to the surface, leaving a clear solution underneath. The clear solution was collected and tested for absorbance measurement at 260 nm using a spectrophotometer (Agilent 8453 UV-VIS spectrophotometer; Agilent Technologies; Santa Clara Calif.) to determine the amount of DNA in the sample after adding glass bubbles as compared to a reference sample before adding the bubbles. The amount of captured DNA is shown in Table 5 in micrograms of DNA per milligram of glass bubbles.

TABLE 5

DNA capture by amine-modified glass bubbles

| Example | Glass bubble preparation | Captured DNA (ug/mg-glass bubble) |
|---|---|---|
| 20 | Example 6  | 0.330 |
| 21 | Example 7  | 0.413 |
| 22 | Example 8  | 0.473 |
| 23 | Example 9  | 0.158 |
| 24 | Example 10 | 0.360 |
| 25 | Example 11 | 0.435 |
| R3 | Example R1 | -0.008 |
| R4 | Example R2 | 0.008 |

Example 26 and Reference Example R5: Protein Capture by Amine-Modified Glass Bubbles 20 milligrams of an amine-coated fractionated glass bubbles from Example 12 were added to a mixture of 1.5 mL of 1 mg/mL BSA (Bovine serum albumin; Sigma-Aldrich; St. Louis, Mo.) in 10 millimolar PBS buffer with the pH was adjusted to 6.0, 7.0 or 8.0, using 0.1 N HCl or 0.1 N NaOH and mixing in a centrifuge tube. Tubes were inverted up and down repeatedly for 2 minutes at room temperature. The tubes were placed upright for approximately 10 seconds for the glass bubbles to float to the surface and leave a clear solution underneath. The clear solution was collected for absorbance measurement at 280 nm using an Agilent 8453 UV-VIS spectrophotometer. Example R5 was prepared with unmodified, fractionated K25 glass bubbles from Example R1.

TABLE 6

BSA capture by amine-modified glass bubbles

| Example | Glass Bubble | pH | Captured BSA (μg of BSA/mg-glass bubbles) |
|---|---|---|---|
| 26 | Example 12 | 6 | 1.84 |
|    |            | 7 | 1.42 |
|    |            | 8 | 1.19 |
| R5 | R1         | 6 | 1.29 |
|    |            | 7 | 0.96 |
|    |            | 8 | 0.17 |

Other embodiments of the invention are within the scope of the appended claims.

What is claimed is:

1. A method for capturing an analyte, the method comprising:
   providing a bioseparation composition comprising:
   a plurality of hollow particles; and
   a surface-modifying agent bonded to the hollow particles, wherein the surface-modifying agent comprises a binding segment and a reactive segment, wherein the-surface-modifying agent comprises an aminosilane;
   wherein the plurality of hollow particles have an average density between about 0.05 and 0.4 g/ml; and
   contacting the bioseparation composition with a solution comprising an analyte, wherein the surface-modifying agent captures the analyte by directly coupling the analyte with the aminosilane.

2. The method of claim 1, further comprising separating the bioseparation composition from the solution.

3. The method of claim 2, wherein separating the bioseparation composition from the solution comprises allowing the bioseparation composition to float to an upper surface of the solution.

4. The method of claim 1, wherein the hollow particles comprise glass bubbles.

5. The method of claim 1, wherein a size distribution of the plurality of hollow particles has a span of less than 1.0.

* * * * *